US012657673B2

(12) United States Patent
Koehler et al.

(10) Patent No.: US 12,657,673 B2
(45) Date of Patent: Jun. 16, 2026

(54) REDUCTION OF ARTEFACTS IN MEDICAL IMAGES

(71) Applicant: KONINKLIJKE PHILIPS N.V., Eindhoven (NL)

(72) Inventors: Thomas Koehler, Norderstedt (DE); Bernhard Johannes Brendel, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 322 days.

(21) Appl. No.: 18/266,071

(22) PCT Filed: Dec. 3, 2021

(86) PCT No.: PCT/EP2021/084163
§ 371 (c)(1),
(2) Date: Jun. 8, 2023

(87) PCT Pub. No.: WO2022/122582
PCT Pub. Date: Jun. 16, 2022

(65) Prior Publication Data
US 2024/0029214 A1       Jan. 25, 2024

(30) Foreign Application Priority Data

Dec. 10, 2020    (EP) ..................................... 20212943

(51) Int. Cl.
*G16H 30/40*          (2018.01)
*G06T 5/77*           (2024.01)
(52) U.S. Cl.
CPC ............... *G06T 5/77* (2024.01); *G16H 30/40* (2018.01); *G06T 2207/10081* (2013.01)

(58) Field of Classification Search
CPC ............. G06T 5/77; G06T 2207/10081; G06T 2207/30004; G06T 5/50; G06T 11/008; G16H 30/40
See application file for complete search history.

(56) References Cited

U.S. PATENT DOCUMENTS 7,623,691 B2      11/2009   Hein
7,894,567 B2 *     2/2011   Hagiwara ............... G06T 12/30
                                                                 378/4

(Continued)

FOREIGN PATENT DOCUMENTS

CN          105678711 A       6/2016
JP          2010022576 A      2/2010

OTHER PUBLICATIONS

PCT International Search Report, International application No. PCT/EP2021/084163, Apr. 7, 2022.

(Continued)

*Primary Examiner* — Incent Rudolph
*Assistant Examiner* — Keely Gwynne Yeargin
(74) *Attorney, Agent, or Firm* — Larry Liberchuk

(57)          ABSTRACT

A mechanism for generating an artefact estimation image that represents the effect of cone-beam artefacts in a computed tomography (CT) image. This is achieved by identifying the position of gradients (being sudden changes of intensity) in an axis of the CT image parallel to a rotation axis of the CT system that generated the CT image, where each gradient represents a source of a cone-beam artefact. A look-up table is used to individually identify the effect of a cone-beam artefact on areas surrounding each identified position of the gradient, to generate an artefact estimation image.

13 Claims, 4 Drawing Sheets

(56) References Cited

U.S. PATENT DOCUMENTS

| 8,831,319 B2 | 9/2014 | Dafni |
| 9,269,128 B2 | 2/2016 | Kim |
| 11,435,419 B2 | 9/2022 | Lingala |
| 2013/0101192 A1 | 4/2013 | Nakanishi |
| 2019/0104940 A1 | 4/2019 | Zhou |

OTHER PUBLICATIONS

Tang X. et al., "On the Data Acquisition, Image Reconstruction, Cone Beam Artifacts, and their suppression in axial MDCT and CBCT—A review", Medical Physics (Lancaster), Sep. 1, 2018 (Sep. 1, 2018), pp. 761-782, XP055806071.
Preuhs A. et al., "Deep Autofocus with Cone-Beam CT Consistency Constraint", Machine Learning (cs.LG), Computer Vision and Pattern Recognition (cs.CV); Image and Video Processing, arXiv.1911.13162v3, Dec. 2019.

* cited by examiner

310

300

320

CT Image — 490

400

Obtain CT Image — 410

440 — Obtain Look-up Table

420 — Identify Position of Gradients

430 — Identify Relative Position of Gradient

450 — Generate Artefact Estimation Image

460 — Generate Artefact Corrected CT Image

470 — Analyse CT Image

REDUCTION OF ARTEFACTS IN MEDICAL IMAGES

FIELD OF THE INVENTION

The present invention relates to the field of medical imaging, and in particular to the reduction of artefacts in medical images.

BACKGROUND OF THE INVENTION

There is an increasing usage of medical images to assess the condition of a patient/individual. Accordingly, there is an increasing desire to reduce any artefacts present in medical images.

One area of medical imaging that is widely used is computed tomography (CT) imaging. Lately, there has been a growing interest in performing CT imaging with a large coverage, where coverage refers to the amount of anatomy being imaged within one rotation of the CT gantry. This type of imaging can be labelled "large coverage CT imaging". Currently, a coverage of no less than 15 cm along the rotation axis of the CT system (e.g. along a vertical axis of the imaged patient) is being targeted. This can facilitate single shot CT imaging without table motion.

One problem with large coverage CT imaging is that it may be unable to provide sufficient data for exact reconstruction of the imaged area. One particular area of concern are artefacts known as cone beam artefacts. A cone beam artefact results is caused by the shape of an x-ray beam becoming cone shaped (rather than fan shaped) as the size of the coverage increases.

There is an ongoing desire to reduce artefacts in CT images.

Patent application US2013/0101192 discloses removal or reduction of cone beam artifacts by reconstructing a reference image from measured data at a circular source trajectory, generating synthetic data by forward projection of the reference image along a pre-determined source trajectory, and reconstructing a correction image.

SUMMARY OF THE INVENTION

The invention is defined by the claims.

According to examples in accordance with an aspect of the invention, there is provided a computer-implemented method of generating an artefact estimation image representing the predicted effect of one or more cone-beam artefacts in a computed tomography image.

The computer-implemented method comprises: obtaining a computed tomography image of an individual; identifying the position of one or more gradients of the computed tomography image, wherein a gradient is a change in the magnitude of pixel values of the computed tomography image, over a predetermined distance in a direction parallel to a first axis of the computed tomography image, greater than a predetermined value, wherein the first axis represents an a rotation axis of the computed tomography system that generated the computed tomography image; identifying, for each gradient, the relative position of the gradient with respect to an artefact estimation image; obtaining a look-up table that correlates a relative position of a gradient with respect to the artefact estimation image with a value that represents a change in intensity value resulting from a cone-beam artefact caused by the gradient (i.e., this value is a predicted effect of a cone-beam artefact to pixels in the artefact estimation image); and generating an artefact estimation image that represents the change of intensity caused by one or more cone-beam artefacts in the computed tomography image, by processing the identified positions of the one or more gradients of the computed tomography image and the look-up table.

The present disclosure proposes an approach for generating an artefact estimation image that represents the predicted effect of cone-beam artefact(s) on a computed tomography image.

A fundamental recognition of the present invention is that reconstruction of a computed tomography image is generally a linear operation. This recognition, in combination with the insight that only gradients in a z-direction of the CT image cause cone-beam artifacts, means that is it possible to utilize a look-up table that effectively identifies the resultant artifacts caused by the gradient(s), e.g. at different locations, within the computed tomography image, i.e. within the field of view presented by the computed tomography image. In particular, it has been recognized that reconstruction is a linear operation, meaning that the principle of superposition can be exploited. Thus, an overall cone beam artifact(s) in a CT image can be represented by a sum of "small" contributions, each contribution generated by or resulting from a gradient in a certain location of the image. Moreover, the artifact strength due to any given gradient scales linearly with the magnitude of this gradient. Thus, if the artifact contribution for a "unit" gradient is known at a certain location in the image, it is possible to scale this artifact contribution to the true contribution to the artefact by the gradient.

In particular, it is recognized that a gradient will act as a "source" of a cone-beam artefact. It is appreciated that the effect of the cone-beam artefact differs based on a distance from and/or a position about the source of the cone-beam artefact, so that an artefact estimation image can be accurately built up using known locations of gradients within the CT image (i.e. known locations of sources) and information that defines how the cone-beam artefact affects a pixel at different positions about and/or distances from the artefact estimation image.

Use of a look-up table avoids the needs for potentially complex and computationally expensive mechanisms for accounting for cone-beam artefacts, such as the use of fast Fourier transforms (FFT) or forward projection and filtered back-projection steps.

The step of identifying the relative position of the gradient with respect to the artefact estimation image may comprise determining a position, in the artefact estimation image, of a gradient mapped from the computed tomography image to the artefact estimation image.

The gradient is mapped from the CT image to the artefact estimation image, i.e. to determine a relative position of the gradient (of the CT image) in the artefact estimation image. If the CT image and the artefact estimation image are of the same resolution, this can be achieved by simply determining the position of the gradient in the CT image. If they are of different resolutions, this step can be achieved by determining a relative position of the gradient in the CT image and determining the corresponding relative position in the artefact estimation image.

The relative position of the gradient in the artefact estimation image may comprise a pixel position of the gradient in the artefact estimation image.

In some examples, the predicted effect of a cone-beam artefact in the artefact estimation image changes responsive to a distance from the relative position of the gradient in the artefact estimation image.

The distance may comprise one or more components indicating a relative distance along a particular axis of the image, such as a first component indicating a relative distance along the first axis, a second component indicating a relative distance along a second axis (perpendicular to the first axis) and a third component indicating a relative distance along a third axis (perpendicular to both the first and second axes). One or more of these components may be omitted, depending upon implementation details.

As another example, the distance may comprise an absolute distance, e.g. a magnitude of the distance.

In some examples, the predicted effect of a cone-beam artefact to pixels in the artefact estimation image changes responsive to a direction, with respect to at least one axis, from the relative position of the gradient in the artefact estimation image. The present invention also recognizes that a cone-beam artefact may not be uniform in all directions from a source of the artefact, e.g. from the gradient. Thus, to improve the accuracy of predicting the effect of a cone-beam artefact a direction from the relative position of the gradient may also be taken into account.

The method may comprise generating a modified computed tomography image by subtracting the artefact estimation image from the computed tomography image. This provides a simple approach for generating a computed tomography image in which the effect of cone-beam artefacts is reduced, or less pronounced.

The method may comprise a step of displaying, at a user interface, the modified computed tomography image. This step would credibly assist a clinician in performing a technical process of analyzing or assessing the condition of a patient, as the modified computed tomography image would have fewer cone-beam artefacts.

In some examples, the step of generating the artefact estimation image comprises: generating an initial artefact estimation image by processing the identified positions of the one or more gradients and the look-up table, wherein the initial artefact estimation image has a different resolution to the computed tomography image; and resampling the initial artefact estimation image to match the resolution of the computed tomography image.

Optionally, the initial artefact estimation image has a lower resolution than the computed tomography image and the step of resampling the initial artefact estimation image comprises upsampling the initial artefact estimation image. This approach facilitates use of a smaller look-up table, as a lower resolution initial artefact estimation image can be initially generated using the look-up table without significantly affecting the accuracy of artefact effect determination. This is because the cone-beam artefacts are of a low frequency (meaning they are less affected by upsampling than high-frequency noise or artefacts).

The step of identifying the position of one or more gradients may comprise: identifying each gradient in the tomography image; selecting a subset of one or more of the identified gradients based on the magnitude of the identified gradients; and identifying the position of the subset of one or more gradients. By only selecting a subset of all possible gradients, the number of calculations to generate an artefact estimation image can be reduced. Preferably, a predetermined portion/percentage of the gradients having the greatest magnitude are selected (e.g. the top 5% or the top 1%). It is recognized that, on average, only the largest gradients contribute to artefacts in the CT image.

The steps of identifying, for each gradient, the relative position of the gradient with respect to an artefact estimation image and generating the artefact estimation image may comprise, for each identified gradient: determining a relative position of the identified gradient in the artefact estimation image based on the position of the gradient in the computed tomography image; and using the look-up table and the determined relative position of the gradient in the artefact estimation image to determine the predicted effect of a cone-beam artefact, having a source represented by the identified gradient, to the pixels of the artefact estimation image, combining the determined predicted effects of any cone-beam artefacts at each pixel of the artefact estimation image to thereby generate the artefact estimation image.

The step of generating the artefact estimation image may further comprise, for each pixel of the artefact estimation image: for each identified gradient, weighting the predicted effect of the cone-beam artefact at the pixel based on the magnitude of the identified gradient. This increases an accuracy of the artefact estimation image, as the magnitude of each gradient indicates or is reactive to the magnitude of the cone-beam artefact resulting from the source. Thus, the artefact estimation image can be constructed from more accurate estimations of the effect of cone-beam artefacts (associated with each separate gradient).

The step of combining the determined predicted effects of any cone-beam artefacts preferably comprises summing the determined predicted effects (for each gradient). This approach takes advantage of the superposition principle employed by CT scanner, which, as recognized by the present disclosure, means that the effect of cone-beam artefacts at any given position in the CT image is a resultant sum of the effect of each individual cone-beam artefact of the CT image at that position.

The step of obtaining a computed tomography image of an individual may comprise: obtaining computed tomography data representing data obtained by a computed tomography scanner before reconstruction of a computed tomography image; and reconstructing the computed tomography image from the computed tomography data using a filtered backpropagation algorithm.

There is also proposed a computer-implemented method for analyzing a computed tomography image, the computed-implemented method comprising: obtaining a computed tomography image and an artefact estimation image for the computed tomography image by performing any previously described method; providing the computed tomography image and the artefact estimation image as input to a machine-learning method; and analyzing the computed tomography image by processing the computed tomography image and the artefact estimation image using the machine-learning method.

There is also proposed a computer program product comprising computer program code means which, when executed on a computing device having a processing system, cause the processing system to perform all of the steps of any herein described method.

There is also proposed a processing system for generating an image representing the predicted effect of one or more cone-beam artefacts in a computed tomography image.

The processing system is configured to: obtain a computed tomography image of an individual; identify the position of one or more gradients of the computed tomography image, wherein a gradient is a change in the magnitude of pixel values of the computed tomography image, over a predetermined distance in a direction parallel to a z-axis of the computed tomography image, greater than a predetermined value; identify, for each gradient, the relative position of the gradient with respect to an artefact estimation image; obtain a look-up table that correlates a relative position of a gradient with respect to the artefact estimation image with a predicted effect of a cone-beam artefact to pixels in the artefact estimation image;

and generate an artefact estimation image that represents a predicted effect of one or more cone-beam artefacts in the computed tomography image, by processing the identified positions of the one or more gradients of the computed tomography image and the look-up table.

The processing system may be adapted to carry out any herein described method and vice versa.

These and other aspects and advantages of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
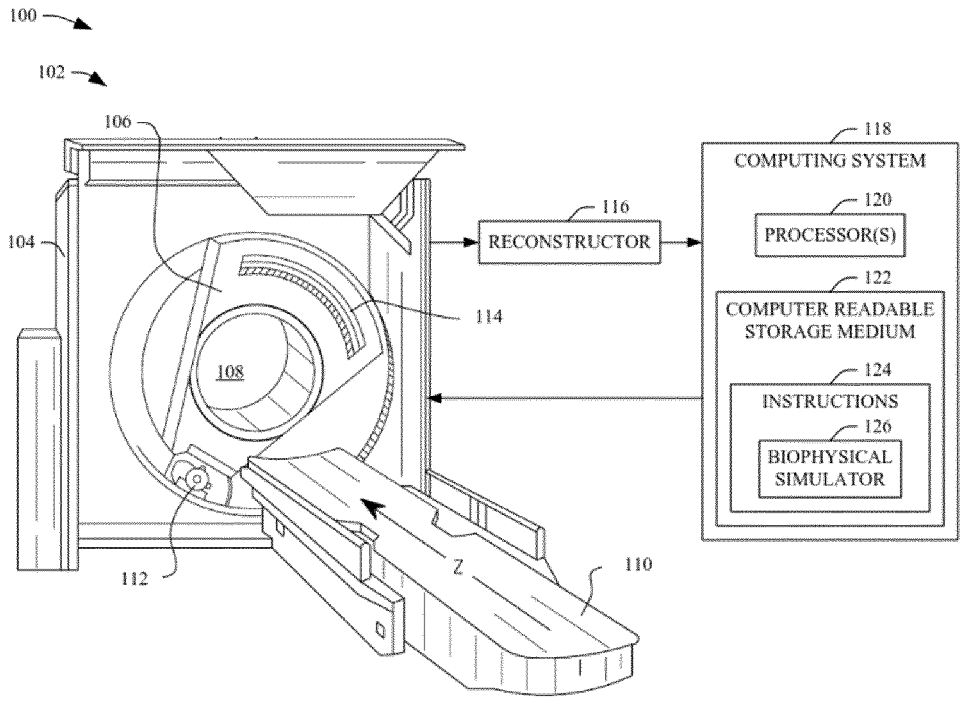
FIG. 1 illustrates a CT system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a mechanism for generating an artefact estimation image that represents the effect of cone-beam artefacts in a computed tomography (CT) image. This is achieved by identifying the position of gradients (being sudden changes of intensity) in an axis of the CT image parallel to a rotation axis of the CT system that generated the CT image, where each gradient represents a source of a cone-beam artefact. A look-up table is used to individually identify the effect of a cone-beam artefact on areas surrounding each identified position of the gradient, to thereby generate an artefact estimation image.

The present disclosure relies upon the realization that reconstruction of a CT image from computed tomography data ("raw data") is a linear operation. This effectively means that the principle of superposition can be exploited, so that each gradient (i.e. representing a source of the cone-beam artefact) can be treated individually, before being combined to generate a single artefact estimation image. Furthermore, it is recognized that the effect of a cone-beam artefact (having a source represented by the gradient) can be approximated based on a position of the gradient in an image.

Embodiments may be employed in any suitable CT imaging system, such as those employed in the healthcare industry, the veterinary industry and/or the archeological industry.

The basic idea employed in this disclosure is the use of a lookup table (LUT) to generate an artifact estimation image. A fundamental insight is that reconstruction techniques used by CT scanner (e.g. a filtered back-projection process) are linear operations. In combination with the insight that only gradients along or in parallel to a rotation axis of the CT system (also called z-axis in the following) cause cone-beam artifacts, it is proposed to build up a LUT that contains the artifacts caused by a gradient. For instance, a LUT may contain the effects (e.g. a value) of cone-beam artifacts for a "unit-gradient" in the z-direction for different locations inside the CT image with respect to other locations inside a CT image.

FIG. 1 schematically illustrates a system 100 including a CT (imaging) system 102 such as a CT scanner. The CT system 102 includes a generally stationary gantry 104 and a rotating gantry 106, which is rotatably supported by the stationary gantry 104 and rotates around an examination region 108 about a z-axis. The CT system 102 also defines an x-axis and a y-axis, both of which are perpendicular to the z-axis and each other. The x-axis lies in a direction generally aligned with gravity (e.g. is vertical), and the y-axis lies in a direction generally parallel with a horizontal plane (i.e. is horizontal). During a medical imaging process, the z-axis usually aligns with a vertical axis of the patient. A subject support 110, such as a couch, supports an object or subject in the examination region 108.

A radiation source 112, such as an x-ray tube, is rotatably supported by the rotating gantry 106, rotates with the rotating gantry 106, and emits radiation that traverses the examination region 108. In one instance, the radiation source 112 includes a single broad spectrum x-ray tube. In another instance, the radiation source 112 includes a single x-ray tube configured to switch between at least two different emission voltages (e.g., 80 kVp and 140 kVp) during scanning. In yet another instance, the radiation source 112 includes two or more x-ray tubes configured to emit radiation having different mean spectra. In still another instance, the radiation source 112 includes a combination thereof.

A radiation sensitive detector array 114 subtends an angular arc opposite the radiation source 112 across the examination region 108. The radiation sensitive detector array 114 detects radiation traversing the examination region 108 and generates an electrical signal(s) (projection data) indicative thereof.

A reconstructor 116 receives projection data from the detector array 114 and reconstructs a CT image such as sCCTA image data, a high-energy image, a low energy image, a photoelectric image, a Compton scatter image, an iodine image, a calcium image, a virtual non-contrast image, a bone image, a soft tissue image, and/or other basis material image.

A computing system 118 serves as an operator console. The console 118 includes a human readable output device such as a monitor and an input device such as a keyboard, mouse, etc. Software resident on the console 118 allows the operator to interact with and/or operate the scanner 102 via a graphical user interface (GUI) or otherwise. The console 118 further includes a processor 120 (e.g., a microprocessor, a controller, a central processing unit, etc.) and a computer readable storage medium 122, which excludes non-transitory medium, and includes transitory medium such as a physical memory device, etc. The computer readable storage medium 122 includes instructions 124 for generating an artefact estimation image and/or processing the CT image. The processor 120 is configured to execute the instructions 124. The processor 120 may additionally be configured to execute one or more computer readable instructions carried by a carrier wave, a signal and/or other transitory medium. In a variation, the processor 120 and the computer readable storage medium 122 are part of another computing system, which is separate from the computing system 118.

Figure 2:
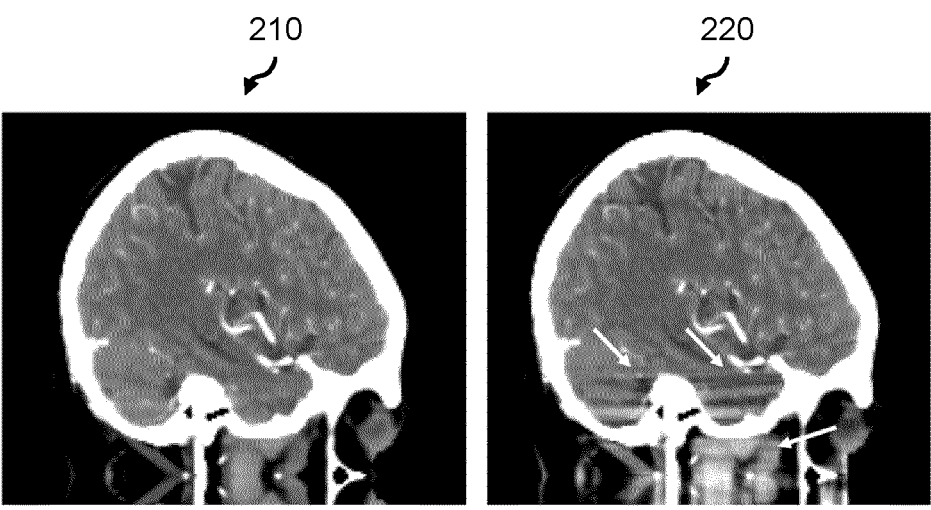
FIG. 2 illustrates the effect of cone-beam artefacts on a CT image.

FIG. 2 illustrates the effect of cone-beam artefacts on a CT image.

A CT image can be associated with a plurality of axes. In particular, a (3D) CT image may have a first axis ("z-axis") which represents (and is aligned with or parallel to) a rotation axis of the CT system that generated the CT image, a second axis ("x-axis") which represents an axis perpendicular to the z-axis and usually represents an gravitational axis, and a third axis ("y-axis") which is perpendicular to both the z and x axes.

Thus, the CT image may be a three-dimensional CT image.

A first CT image 210 illustrated by FIG. 2 illustrates a CT image captured with no cone-beam artefacts. This can be achieved, for instance, by performing CT imaging using a directed beam, having low beam coverage (e.g. <5 cm) along the rotation axis of the CT system, i.e. where the beams emitted during the CT scan can be modeled using a fan-beam rather than a cone-beam.

A second CT image 220 illustrated by FIG. 2 depicts a CT image reconstructed from an axial cone-beam CT scan. The second CT image has cone-beam artefacts. These artefacts are caused by sudden changes in density of a region being imaged (e.g. a sudden change from brain matter to bone at the base of the skull). Cone-beam artefacts are only produced by sudden changes along an axis aligned with (i.e. representing) the rotation axis of the CT system generating the CT image (the "z-axis"). This is because standard reconstruction algorithms are designed such that they provide exact reconstruction if the object is homogenous in this z-axis. Thus, the "source" of a cone-beam artefact in a CT image can be represented by a sudden gradient along the axis of the CT image representing the rotation axis of the CT system.

A sudden gradient may be defined, for instance, as a change in the magnitude of pixel values of the computed tomography image, over a predetermined distance in a direction parallel to a first axis of the computed tomography image, greater than a predetermined value. The first axis is the axis of the CT image representing the rotation axis of the CT system, i.e. the z-axis.

Figure 3:
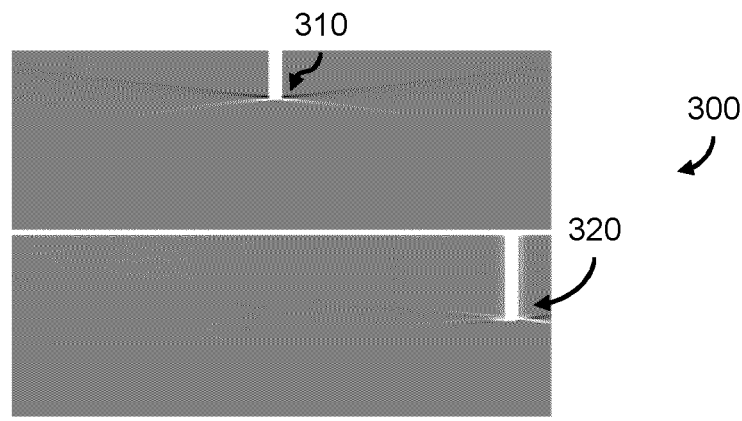
FIG. 3 also illustrates the effect of a cone-beam artefact on a CT image.

FIG. 3 also illustrates the effect of a gradient 310, 320 (representing a source of cone-beam artefacts) on other parts of an image 300. The pixel values for the image 300 are uniform, except at locations representing a gradient and locations representing areas modified as a result of one or more cone-beam artifacts having a source represented by the gradient.

FIG. 3 clearly illustrates how the cone-beam artefact "spreads out" from the position of the gradient 310, 320. Thus, the magnitude of the effect of the cone-beam artefact at any given pixel of the image is dependent upon at least a direction between the given pixel and the gradient and a distance between the given pixel and the gradient.

The present invention exploits this recognition to provide a look-up table that can be used to estimate or predict the effect of each gradient on a CT image, and thereby generate an artefact estimation image that predicts the effect of each gradient on the CT image.

Figure 4:
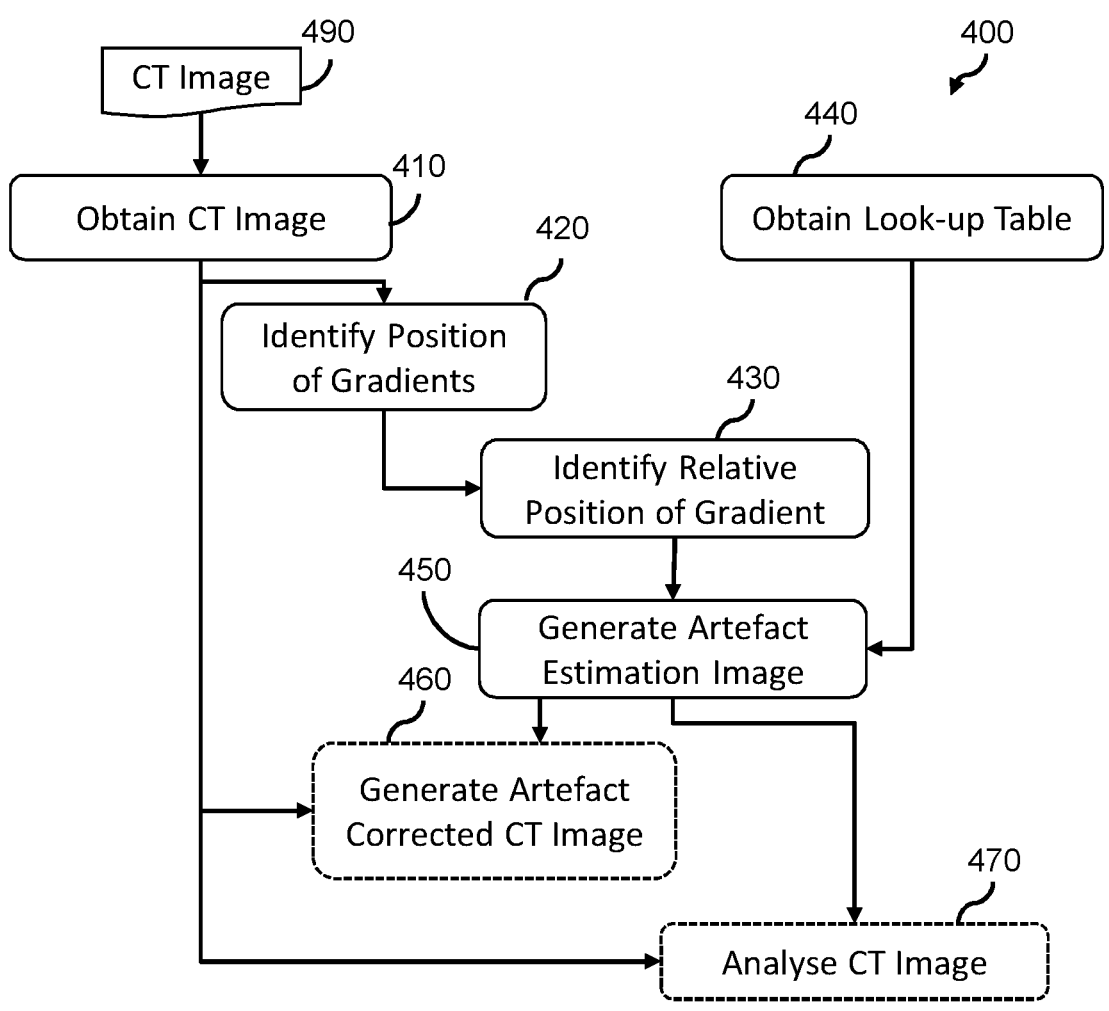
FIG. 4 illustrates a method.

FIG. 4 illustrates a method 400 according to an embodiment of the invention. The method 400 is configured to generate an artefact estimation image that represents the predicted cone-beam artefacts in a computed tomography (CT) image.

The method 400 comprises a step 410 of obtaining the computed tomography (CT) image 490 of the subject. The CT image may be obtained from a CT system, such as that described with reference to FIG. 1, or from a database or memory. The CT image is an image that has been reconstructed from raw or projection data generated by a CT system.

The method then comprises a step 420 of identifying the position of one or more gradients in the CT image. A gradient represents a sudden change of intensity in the CT image in a direction aligned (i.e. parallel with) an axis representing a rotation axis of the CT system, i.e. an axis about which a CT gantry rotates, usually labelled the "z-axis". The identified position may correlate to a particular pixel position of the gradient, e.g. a pixel position of a pixel that is part of the identified gradient, e.g. using an appropriate co-ordinate system for the CT image (e.g. using x,y,z co-ordinates or using relative positions, e.g. percentages to identify a relative position within the CT image).

Appropriate image processing techniques for identifying such a gradient would be readily apparent to the skilled person. In particular, a gradient can be represented by a change in the magnitude of pixel values of the computed tomography image, over a predetermined distance in a direction parallel to a first axis of the computed tomography image, greater than a predetermined value.

In one example, step 420 comprises identifying the position of all gradients in the CT image, and subsequently selecting only a subset of the gradients for further processing (i.e. during the method 400). The selected subset may include, for instance, the gradients having the highest magnitudes (e.g. the largest X % of gradients, where X is a predetermined value such as 1 or 5, or gradients above a certain threshold). The magnitude of a gradient may be defined as the difference in magnitude of pixel values over the predetermined distance of the gradient. This approach means that only the strongest gradients are further processed, which saves computational complexity. The present disclosure recognizes that the contribution of the gradients having the highest magnitudes represents the majority of the cause of cone-beam artefacts, so that an accurate artefact estimation image can be generated from the top gradients without affecting the accuracy of the artefact estimation images.

The method 400 further comprises a step 430 of identifying, for each gradient, the relative position of the gradient with respect to an artefact estimation image.

In particular, the spatial relationship between positions in the CT image and positions in the artefact estimation image may be known or predetermined. This facilitates identification of where each gradient would appear in the artefact estimation image if it were to be mapped to the artefact estimation image.

Step 430 may therefore comprise determining a (pixel) position, in the artefact estimation image, of a gradient mapped from the computed tomography image to the artefact estimation image.

For instance, if the CT image is a 3D image having a resolution of 1600×1200×800, the artefact estimation image has a resolution of 400×300×200 and the position of the gradient in the CT image is located at a pixel at location 1000, 800, 100—then the relative position of the gradient in the artefact estimation image is at position 250, 200, 25.

It should be appreciated that the area covered by the CT image and the artefact estimation image (e.g. the relative size of the "CT scan area" covered) is identical.

The artefact estimation image has a same number of dimensions as the CT image. The resolution of the artefact estimation image may be different to the resolution of the CT image, and is preferably smaller. However, in other embodiments, the resolution of the artefact estimation image may be identical to the resolution of the CT image, and step 430 may form part of step 420 (as identifying the position of the gradient(s) in the CT image would now be functionally equivalent to identifying the position of the gradient(s) in the artefact estimation image).

The method 400 further comprises a step 440 of obtaining a look-up table that correlates a relative position of a gradient with respect to the artefact estimation image with a predicted effect of a cone-beam artefact to pixels in the artefact estimation image.

The look-up table thereby effectively identifies, for each pixel in the artefact estimation image, the effect resulting from a cone-beam artefact having a source at different relative positions for a gradient in the artefact estimation image. The effect may, for instance, be a value that represents (e.g. is) a change in intensity value resulting from a cone-beam artefact having a source represented by a gradient (e.g. of a predetermined magnitude).

It is an underlying recognition of the present invention that the (relative) effect of a source of cone-beam artefacts, represented by a gradient, in any given image to any given pixel of that image ("particular pixel") can be estimated based on the position of the gradient in the image and the position of the particular pixel.

Thus, a look-up table can be used to generate an artefact estimation image that estimates the effect of a source of cone-beam artefacts on different pixels of a CT image. For instance, the position of gradients in the CT image can be mapped or registered to relative positions in an artefact estimation image. The lookup table may then be able to provide, for each other pixel of the artefact estimation image, the relevant information for identifying an effect of the cone-beam artefact at that position. This means that an artefact estimation image can be generated from the CT image using the look-up table.

The method 400 also comprises a step 450 of generating an artefact estimation image that represents a predicted effect of one or more cone-beam artefacts in the computed tomography image, by processing the identified positions of the one or more gradients of the computed tomography image and the look-up table.

More complete working examples of the proposed approach for using a look-up table, as well as examples of suitable look-up tables, will be described later.

The artefact estimation image thereby provides information on the estimated effect of cone-beam artefacts on a CT image 490. In particular, the artefact estimation image by itself provides useful clinical information, by identifying the presence of possible artefacts in the CT image to reduce the likelihood that artefacts will be misattributed to features of the imaged patient and/or to reduce masking of potentially important features by artefacts.

The artefact estimation image thereby effectively represents the end result of an artefact-identifying process, to identify the effect of cone-beam artefacts in a CT image.

In some examples, the artefact estimation image and the CT image may be processed and/or combined in a step 460 to generate a corrected CT image. For instance, the artefact estimation image (which, if necessary, may be scaled/resampled to match a resolution of the CT image) may be subtracted from the CT image to generate a corrected CT image. This produces a CT image with reduced cone-beam artefacts.

In some examples, the artefact estimation image and the CT image are provided as input data for an analysis process, e.g. one that employs a machine-learning algorithm to analyze and/or classify the CT image in a step 470. This provides the analysis process with additional information for processing a CT image, providing additional features that result in improved analysis of the CT image (e.g. to avoid unintentionally attributing artefacts to particular characteristics or features of the CT image).

It has been explained how the generation of the artefact estimation image makes use of a look-up table, and the determined position of the gradients in the CT image, to generate the artefact estimation image.

Generally, a look-up table is an array that correlates predetermined input values with predetermined output values. In particular, a look-up table will provide for each of a plurality of input values, or combinations of input values, an associated predetermined output value (or values). In other words, the look-up table defines, for different combinations of values of one or more input parameters, one or more values for an output parameter.

For the present disclosure, a lookup table correlates a relative position of a gradient in the artefact estimation image, with an effect of a cone-beam artefact (across the other pixels of the artefact estimation image) having a source at the relative position of the gradient.

Thus, for each of a plurality of different possible positions for the gradient with respect to the artefact estimation image, the lookup table may provide a value for each (other) pixel in the artefact estimation image that predicts the effect (e.g. in the form of a value) of a cone-beam artefact having a source at the relative position of the gradient. In particular, the value may represent an effect of a cone-beam having a source represented by a gradient having a predetermined magnitude (i.e. a "unity gradient" or a "normalized gradient") in the image.

An effect may comprise a value representing the predicted change in intensity value (for a pixel of a CT image), e.g. in terms of percentage or absolute change value, that results from a cone-beam artefact having a source represented by a gradient at a particular relative position of the artefact estimation image.

As a whole, the lookup table therefore effectively stores an artefact pattern that identifies, for different possible (pixel) positions for gradients in the artefact estimation image, the effect of a cone-beam artefact across all other pixels of the image.

The present disclosure recognizes that the effect of a single cone-beam artefact (having a source represented by a single pixel) at any given pixel of the artefact estimation image depends upon the relative location of the gradient in the artefact estimation image and the positional relationship between the pixel and the gradient.

In any given image, the effect of a cone-beam artefact changes with distance and/or direction from the source of the artefact and position of the gradient (representing a source of the artefact) within an image.

It is also appreciated that gradients in a CT image may have different magnitudes or strengths, where the magnitude or strength of the gradient influences the effect that the gradient will have on cone-beam artefacts found in the CT image. Use of a predetermined magnitude for the gradient (modelled by the look-up table) means that the true effect of a gradient in the CT image can be subsequently calculated (e.g. by suitable weighting of the determined effect based on a relationship between the magnitude of the gradient in the CT image and the predetermined magnitude).

Thus, the look up table can provide a "normalized" value for the effect resulting from the gradient.

Figure 5:
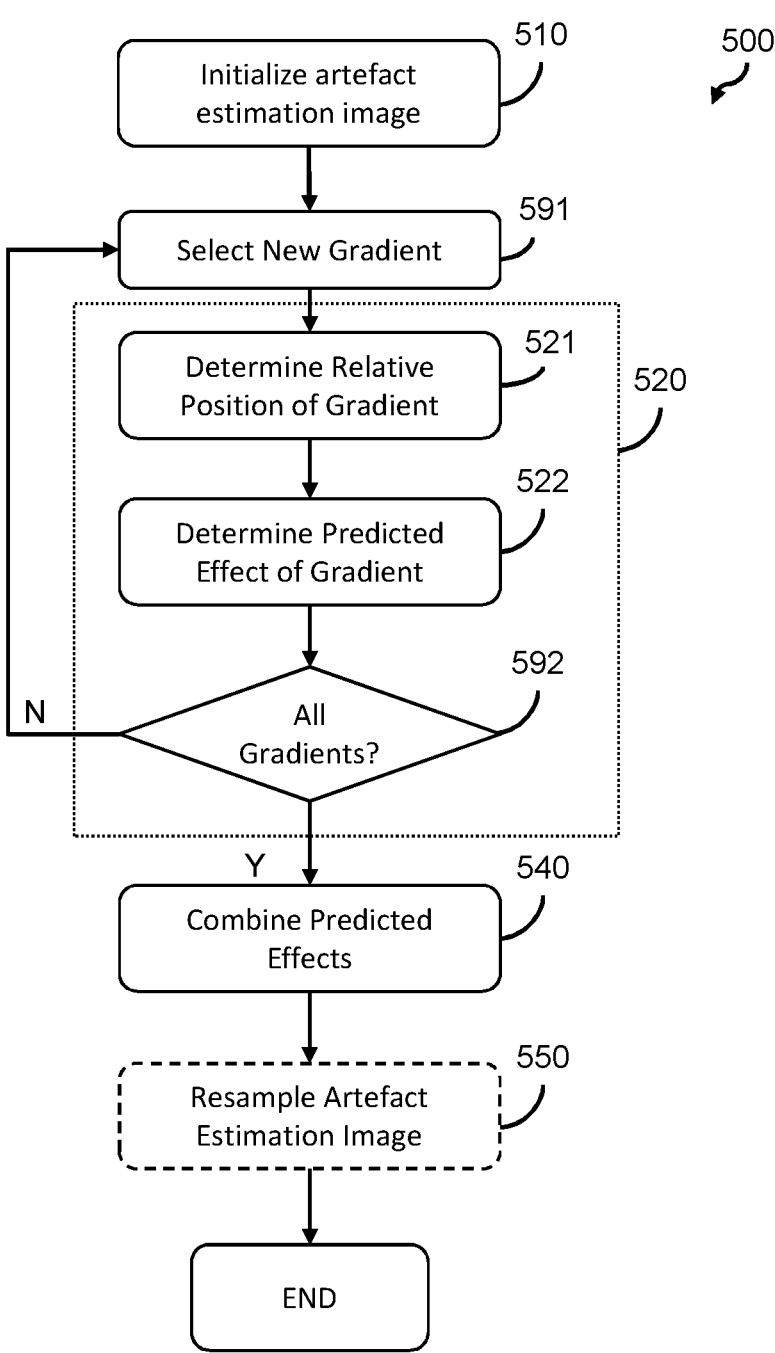
FIG. 5 illustrates a process for the method.

FIG. 5 illustrates a method for generating an artefact estimation image using a lookup table and the identified positions of the gradient(s) determined in step 420 in the CT image. This is an example of steps 430, 440 and 450 described with reference to FIG. 4.

The method 500 comprises a step 510 of initializing the artefact estimation image, e.g. generating an "initial artefact estimation image". The initial artefact estimation image is generated so that a spatial relationship between positions in the CT image and positions in the artefact estimation image is known. The resolution of the initialized artefact estimation image may be different to the resolution of the CT image, and is preferably smaller. The artefact estimation image has a same number of dimensions as the CT image.

Thus, the position of an element, particularly a gradient, of the CT image may be mapped to a corresponding position in the artefact estimation image. In this way, a relative position of a gradient (of the CT image) in the artefact estimation image can be calculated or determined.

The method 500 then executes a process 520 which is performed for each gradient identified in the CT image in step 420. This is illustrated through steps 591, which selects a new (i.e. not yet processed for that pixel) gradient, and step 592, which determines if all identified gradients have undergone process 520 and, if not, reverts back to step 591 to select a new gradient or else ends the iterations of process 520 for the pixel.

The process 520 comprises a step 521 of determining a relative position of the gradient in the artefact estimation image based on the position of the gradient in the computed tomography image. This is achievable when a spatial relationship between the CT image and the artefact estimation image is known or predetermined, e.g. the CT image and the artefact estimation image are registered with respect to one another.

The process 520 then comprises a step 522 of using the look-up table and the relative position of the gradient in the artefact estimation image, to determine the effect of a cone-beam artefact at each pixel position (of the artefact estimation image). This may be performed on a pixel by pixel basis (e.g. if the look-up table identifies, for each pixel of the artefact estimation image, the effect of the cone-beam artefact) or on a whole artefact estimation image basis.

Once process 520 has been performed for each identified gradient, the process 500 then performs a step 540 of combining the predicted effects determined for each gradient to determine an overall effect of cone-beam artefacts at the pixel. This may comprise, for instance, summing the determined effects (for each pixel) to determine the overall effect. This makes use of the principle of superposition, namely that the overall effect of a cone-beam artefact results from the combined contribution of cone-beam artefacts resulting of all gradients in the image.

Preferably, the step 522 of determining the predicted effect of the cone-beam artefact comprises identifying the effect indicated (for each pixel of the artefact estimation image) by the look-up table, and weighting or modifying the indicated effects based on a magnitude of the gradient (of the CT image). In particular, the greater the magnitude of the gradient (e.g. the greater the difference in intensity values at a position of the gradient) the greater the effect is weighted.

This embodiment takes into account the relative magnitude/strength of a gradient. It is appreciated that the greater the relative magnitude, the greater the impact that the gradient will have on cone-beam artefacts in the CT image.

A simple method for performing this step could be to weight (e.g. multiply) the determined effect of the gradient (as set out in the look-up table) by a value equal to the magnitude of the gradient (in the CT image) divided by the magnitude of the gradient used to generate the look-up table.

In some examples, the step of generating the artefact estimation image comprises generating an initial artefact estimation image by processing the identified positions of the one or more gradients and the look-up table, wherein the initial artefact estimation image has a different resolution to the computed tomography image; and resampling the initial artefact estimation image to match the resolution of the computed tomography image.

Thus, the method 500 may further comprise a step 550 of resampling the artefact estimation image output by step 540. As previously explained, the initialized artefact estimation image may have a different resolution to the CT image. This approach of generating an artefact estimation image, and resampling the artefact estimation image allows for reduced processing complexity and memory space requirements for the look-up table and when generating the initial artefact estimation image.

Preferably, the artefact estimation image has a lower resolution than the CT image. This is achievable without significantly affecting an accuracy of the artefact estimation image because the artefacts are low frequency, meaning that fewer entries for the lookup table are required.

Various mechanisms for reducing or minimizing a necessary size of the look-up table are envisaged. For instance, symmetries of the cone-beam effect can be assumed and exploited to reduce the size of the look-up table.

As one example, the present invention recognizes that the effect of a gradient is invariant with respect to distance of the gradient from the z-axis (i.e. the axis aligned with a rotation of the CT gantry). This is because the cone-beam artefact is invariant with respect to rotation around the z-axis.

Thus, it is only necessary to provide a lookup table that provides the effect (on pixels of the artefact estimation image) for gradients in a single plane passing through the z-axis (e.g. an xz plane or an yz plane). When using the LUT table to determine the effect of gradients outside of this plane, we can "rotate" the gradient (around the z-axis) until it falls in this plane, determine the relevant effect for the artefact estimation image and "rotate" the effect back. Appropriate methods for rotating locations from one position to another will be readily apparent to the skilled person, e.g. using standard rotation mechanics for image processing.

Moreover, it is also recognized that the effect of a gradient is symmetrical for gradients above and below a plane of rotation (if data acquisition with the CT system is done rotating the gantry by 360° without moving the patient support). That is, the effect for a gradient at a first z-axis distance above a first point on plane of rotation (e.g. the xy plane) is the mirror of the effect of a gradient at the same distance below the plane of rotation.

Thus, it is only necessary for the lookup table to store the effect of gradients lying either above below the plane of rotation. When using the LUT to determine the effect of gradients at the other of above or below, we may determine the mirror position (through a mirror lying in the plane of rotation) of the gradient, identify the effect of for the artefact estimation image, and mirror the determined effect back.

The look-up table may be compressed, according to known compression principles. This is because the effect of a gradient (in an image) on a large number of pixels of the image is expected to be negligible or zero. Thus, the look-up table can be appropriately compressed without any or without significant loss of accuracy.

Figure 6:
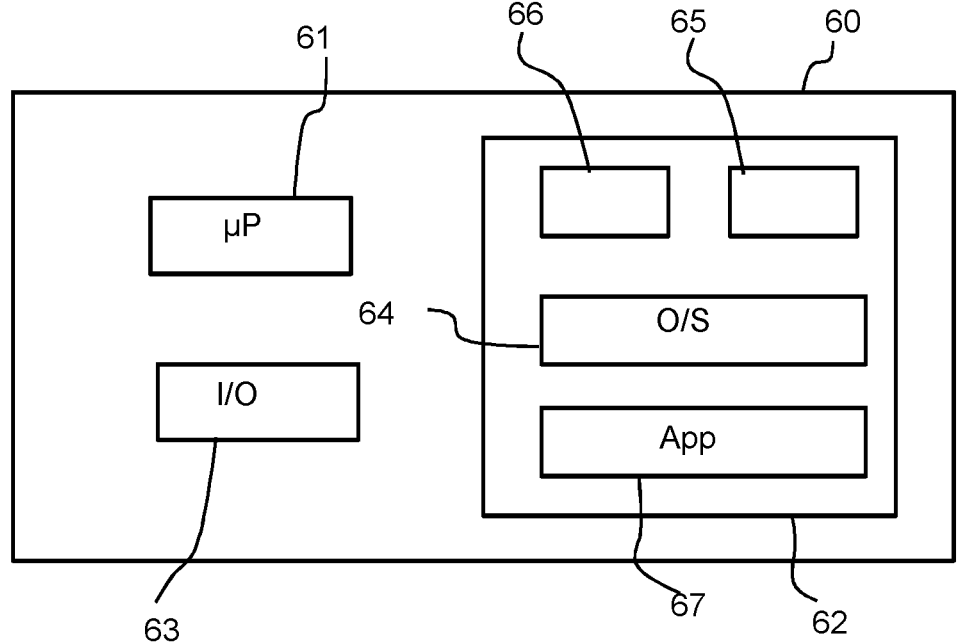
FIG. 6 illustrates a processing system.

By way of further example, FIG. 6 illustrates an example of a processing system 60 within which one or more parts of an embodiment may be employed. Various operations discussed above may utilize the capabilities of the processing system 60. For example, one or more parts of a system for generating an artefact estimation image may be incorporated in any element, module, application, and/or component discussed herein. In this regard, it is to be understood that system functional blocks can run on a single computer or may be distributed over several computers and locations (e.g. connected via internet).

The processing system 60 includes, but is not limited to, PCs, workstations, laptops, PDAs, palm devices, servers, storages, and the like. Generally, in terms of hardware architecture, the processing system 60 may include one or more processors 61, memory 62, and one or more I/O devices 67 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 61 is a hardware device for executing software that can be stored in the memory 62. The processor 61 can be virtually any custom made or commercially available processor, a central processing unit (CPU), a digital signal processor (DSP), or an auxiliary processor among several processors associated with the processing system 60, and the processor 61 may be a semiconductor based microprocessor (in the form of a microchip) or a microprocessor.

The memory 62 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 62 may incorporate electronic, magnetic, optical, and/or other types of storage media. Note that the memory 62 can have a distributed architecture, where various components are situated remote from one another, but can be accessed by the processor 61.

The software in the memory 62 may include one or more separate programs, each of which comprises an ordered listing of executable instructions for implementing logical functions. The software in the memory 62 includes a suitable operating system (O/S) compiler 64, source code 63, and one or more applications 66 in accordance with exemplary embodiments. As illustrated, the application 66 comprises numerous functional components for implementing the features and operations of the exemplary embodiments. The application 66 of the processing system 60 may represent various applications, computational units, logic, functional units, processes, operations, virtual entities, and/or modules in accordance with exemplary embodiments, but the application 66 is not meant to be a limitation.

The operating system 65 controls the execution of other computer programs, and provides scheduling, input-output control, file and data management, memory management, and communication control and related services. It is contemplated by the inventors that the application 66 for implementing exemplary embodiments may be applicable on all commercially available operating systems.

Application 66 may be a source program, executable program (object code), script, or any other entity comprising a set of instructions to be performed. When a source program, then the program is usually translated via a compiler (such as the compiler 64), assembler, interpreter, or the like, which may or may not be included within the memory 62, so as to operate properly in connection with the O/S 65. Furthermore, the application 66 can be written as an object oriented programming language, which has classes of data and methods, or a procedure programming language, which has routines, subroutines, and/or functions, for example but not limited to, C, C++, C #, Pascal, BASIC, API calls, HTML, XHTML, XML, ASP scripts, JavaScript, FORTRAN, COBOL, Perl, Java, ADA, .NET, and the like.

The I/O devices 67 may include input devices such as, for example but not limited to, a mouse, keyboard, scanner, microphone, camera, etc. Furthermore, the I/O devices 67 may also include output devices, for example but not limited to a printer, display, etc. Finally, the I/O devices 67 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 67 also include components for communicating over various networks, such as the Internet or intranet.

If the processing system 60 is a PC, workstation, intelligent device or the like, the software in the memory 62 may further include a basic input output system (BIOS) (omitted for simplicity). The BIOS is a set of essential software routines that initialize and test hardware at startup, start the O/S 65, and support the transfer of data among the hardware devices. The BIOS is stored in some type of read-only-memory, such as ROM, PROM, EPROM, EEPROM or the like, so that the BIOS can be executed when the processing system 60 is activated.

When the processing system 60 is in operation, the processor 61 is configured to execute software stored within the memory 62, to communicate data to and from the memory 62, and to generally control operations of the processing system 60 pursuant to the software. The application 66 and the O/S 65 are read, in whole or in part, by the processor 61, perhaps buffered within the processor 61, and then executed.

When the application 66 is implemented in software it should be noted that the application 66 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 66 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

A single processor or other unit may fulfill the functions of several items recited in the claims. A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to". Any reference signs in the claims should not be construed as limiting the scope.

The invention claimed is:

1. A computer-implemented method for generating an artefact estimation image representing a predicted effect of a cone-beam artefact in a computed tomography image, the computer-implemented method comprising:

obtaining the computed tomography image;

identifying a position of one or more gradients of the computed tomography image over a distance in a direction parallel to a Z axis of the computed tomography image that is greater than a predetermined value, wherein a gradient is a change in a magnitude of pixel values of the computed tomography image;

identifying, for each of the one or more gradients, the position with respect to the artefact estimation image;

obtaining a look-up table that correlates the position of each of the one or more gradients with respect to the artefact estimation image with a value that represents a change of intensity value resulting from the cone-beam artefact caused by each of the one or more gradients; and generating the artefact estimation image that represents the change of intensity caused by the cone-beam artefact in the computed tomographyCT image by processing the position of each of the one or more gradients of the computed tomography image and the look-up table.

2. The computer-implemented method of claim 1, wherein identifying the position of each of the one or more gradients with respect to the artefact estimation image comprises determining the position, in the artefact estimation image, of each of the one or more gradients mapped from the computed tomography image to the artefact estimation image.

3. The computer-implemented method of claim 2, wherein the position of each of the one or more gradients in the artefact estimation image comprises a pixel position of each of the one or more gradients in the artefact estimation image.

4. The computer-implemented method of claim 1, wherein the predicted effect of thea cone-beam artefact to pixels in the artefact estimation image changes responsive to the distance from the position of each of the one or more gradients in the artefact estimation image.

5. The computer-implemented method of claim 1, wherein the predicted effect of the cone-beam artefact to pixels in the artefact estimation image changes responsive to the direction, with respect to at least one axis, from the position of each of the one or more gradients in the artefact estimation image.

6. The computer-implemented method of claim 1, further comprising generating a modified computed tomography image by subtracting the artefact estimation image from the computed tomography image.

7. The computer-implemented method of claim 1, wherein generating the artefact estimation image comprises:

generating an initial artefact estimation image by processing the position of each of the one or more gradients and the look-up table, wherein the initial artefact estimation image has a different resolution than the computed tomography image; and resampling the initial artefact estimation image to match the resolution of the computed tomography image.

8. The computer-implemented method of claim 7, wherein the initial artefact estimation image has a lower resolution than the computed tomography image and resampling the initial artefact estimation image comprises upsampling the initial artefact estimation image.

9. The computer-implemented method of claim 1, wherein identifying the position of one or more gradients comprises:

identifying each of the one or more gradients in the computed tomography image;

selecting a subset of the one or more gradients based on a magnitude of each of the one or more gradients; and identifying the position of the subset.

10. The computer-implemented method of claim 1, wherein identifying, for each of the one or more gradients, the position with respect to the artefact estimation image and generating the artefact estimation image comprise:

for each of the one or more gradients:

determining the position of each of the one or more gradients in the artefact estimation image based on the position of each of the one or more gradients in the computed tomography image; and using the look-up table and the position of each of the one or more gradients in the artefact estimation image to determine the predicted effect of the cone-beam artefact, having a source represented by each of the one or more gradients, to pixels of the artefact estimation image, combining the predicted effect of the cone-beam artefact at each pixel of the artefact estimation image to generate the artefact estimation image.

11. The computed-implemented method of claim 10, wherein generating the artefact estimation image comprises, for each of the one or more gradients, weighting the predicted effect of the cone-beam artefact based on athe magnitude of each of the one or more gradients.

12. A computer-implemented method for analyzing a computed tomography image, the computed-implemented method comprising:

obtaining the computed tomography image and an artefact estimation image for the computed tomography image by:

identifying a position of one or more gradients of the computed tomography image over a distance in a direction parallel to a Z axis of the computed tomographyCT image that is greater than a predetermined value, wherein a gradient is a change in a magnitude of pixel values of the computed tomography image;

identifying, for each of the one or more gradients, the position with respect to the artefact estimation image;

obtaining a look-up table that correlates the position of each of the one or more gradients with respect to the artefact estimation image with a value that represents a change of intensity value resulting from the cone-beam artefact caused by each of the one or more gradients; and generating the artefact estimation image that represents the change of intensity caused by the cone-beam artefact in the computed tomography image by processing the position of each of the one or more gradients of the computed tomography image and the look-up table;

providing the computed tomography image and the artefact estimation image as input to a machine-learning model; and analyzing the computed tomography image by processing the computed tomography image and the artefact estimation image using the machine-learning model.

13. A computer-implemented processing system for generating an artefact estimation image representing a predicted effect of a cone-beam artefact in a computed tomography image, the processing system comprising:

a memory that stores a plurality of instructions; and a processor coupled to the memory and configured to execute the plurality of instructions to:

obtain the computed tomography image;

identify a position of one or more gradients of the computed tomography image over a distance in a direction parallel to a z-axis of the computed tomography image that is greater than a predetermined value, wherein a gradient is a change in a magnitude of pixel values of the computed tomography image;

identify, for each of the one or more gradients, the position with respect to the artefact estimation image;

obtain a look-up table that correlates the position of each the one or more gradients with respect to the artefact estimation image with a value that represents a change of intensity value resulting from the cone-beam artefact caused by each of the one or more gradients; and generate the artefact estimation image that represents the change of intensity caused by the cone-beam artefact in the computed tomography image by processing the position of each of the one or more gradients of the computed tomography image and the look-up table.

* * * * *